United States Patent [19]

Schwalbach

[11] 4,377,727
[45] Mar. 22, 1983

[54] STETHOSCOPE HAVING MEANS FOR MEASURING PULSE FREQUENCY

[76] Inventor: Joseph C. Schwalbach, 6455 La Jolla Blvd., La Jolla, Calif. 92037

[21] Appl. No.: 220,136
[22] Filed: Dec. 24, 1980
[51] Int. Cl.³ .............................................. A61B 5/02
[52] U.S. Cl. ................................................. 179/1 ST
[58] Field of Search ..................................... 179/1 ST

[56] References Cited

U.S. PATENT DOCUMENTS 1,686,138 10/1928 Marvel .............................. 179/1 ST Primary Examiner—George G. Stellar
Attorney, Agent, or Firm—Joseph C. Schwalbach

[57] ABSTRACT

An improved stethoscope having means for measuring the frequency of a series of pulses, such as human heart pulses, is disclosed, in the use of which such pulses are detected simultaneously with detection of a series of timed detectable reference impulses produced by a reference impulse producer having means for adjusting the frequency of the reference impulses produced thereby and also having readout means indicating the frequency of the reference impulses, wherefore upon adjustment of the frequency of the reference impulses as necessary to match that of said pulses, the frequency of said pulses is indicated on the readout means.

8 Claims, 2 Drawing Figures

U.S. Patent  Mar. 22, 1983  4,377,727

STETHOSCOPE HAVING MEANS FOR MEASURING PULSE FREQUENCY

BACKGROUND OF THE INVENTION

This invention relates to a method and apparatus for measuring the frequency of a series of pulses. There are a number of situations in which it is desirable to measure the cadence or rate of occurrence, i.e. the frequency, of a train of pulses having a usually regular spacing therebetween. Examples of such pulses are the human heartbeat, engine sounds, or in the successive impacts of one machinery part upon another.

Measurement of the frequency of the human heartbeat is routinely undertaken during the course of physical examinations. During such examinations the physician uses a stethoscope to listen to the sounds of the heart and other areas of the patient's body, and while listening to the heart, the physician commonly measures the pulse rate by counting the number of pulses heard within a timed interval during which his attention is focused on his watch or other time measuring means.

A variety of instruments have been developed in the prior art for the measurement of the pulse frequency of humans, ranging from mechanical devices, through electronic listening devices, to the present day sophisticated EKG instrumentation which provides continuous digital readout of the pulse frequency while recording an EKG tracing.

U.S. Pat. No. 1,675,799 discloses a mechanism intended to indicate the pulse frequency of a human being by the use of oscillating bodies consisting of timed frequency tongues, flywheels or pendulums, U.S. Pat. No. 2,831,479 discloses an instrument which utilizes a microphone adapted to be placed on the chest of a patient, a timer presettable to measure a predetermined time interval, and an electromechanical pulse counter operable to indicate the number of pulses detected through the microphone during the interval for which the timer is set.

Other listening type devices of the prior art include the heartbeat frequency analyzer disclosed in U.S. Pat. No. 3,171,406 which electronically indicates the frequency components of a heartbeat to permit early detection of a heart malfunction; the acoustic and electronic stethoscope disclosed in U.S. Pat. No. 3,247,324 which provides amplification of a selected range of frequencies; and the stethoscope with display disclosed in U.S. Pat. No. 3,858,005 wherein the heart or other body sounds are converted to electrical signals which are amplified and fed to a cathode ray tube for visual display of such sounds.

EKG type instrumentation has also been the subject of developments concerned with human heartbeat rate monitoring. U.S. Pat. Nos. 3,595,219 and 3,613,670 disclose EKG tupe instruments which provide audible or visual signals when the heartbeat rate of the patient is below or above a predetermined rate or rate range.

U.S. Pat. No. 3,830,227 discloses a portable electrocardiophone which produces an audible tone pattern which can be audibly analyzed to identify and diagnose various known types of heart arrhythmias. This patent also makes reference to previously developed portable devices which produce a flashing light or audible beep to represent the heartbeat rate. U.S. Pat. No. 3,455,293 discloses a stethoscope providing for electrical connection between the pickup head thereof and an associated EKG machine, which connection permits the physician to listen to a patient's heart at the same time an EKG tracing of the heart action is made.

In spite of all of the developments in stethoscopes and heart rate monitoring instrumentation which have taken place, no apparatus has been developed which provides the functions and portability of a stethoscope and by which pulse frequency can be measured without requiring the physician to count pulses or measure the time.

It is therefore a general object of the present invention to provide an improved stethoscope by the use of which a physician can measure pulse frequency without having to count pulses or measure the time.

Another object of the invention is to provide an improved stethoscope which is simple to use and, in fact, can be used by medically untrained personnel, including the patient himself.

A further object of the invention is to provide an improved stethoscope which in one form thereof permits measurement of pulse frequency by listening to audible signals and reference impulses, and in another form thereof permits such measurement by observation of visual signals and reference impulses, the features of such stethoscopes which permit such measurement, in neither form, interfering with the normal use of such stethoscope.

SUMMARY OF THE INVENTION

The invention comprises an improved stethoscope having means for measuring the frequency of a series of pulses and which permits the pulses to be detected simultaneously with detection of a series of timed detectable reference impulses produced by a reference impulse producer having means for adjusting the frequency of the reference impulses produced thereby and also having readout means indicating the frequency of the reference impulses, wherefore upon adjustment of the frequency of the reference impulses as necessary to match that of the pulses being measured, the frequency of said pulses is indicated on the readout means.

DESCRIPTION OF THE PREFERRED EMBODIMENT

Figure 1:
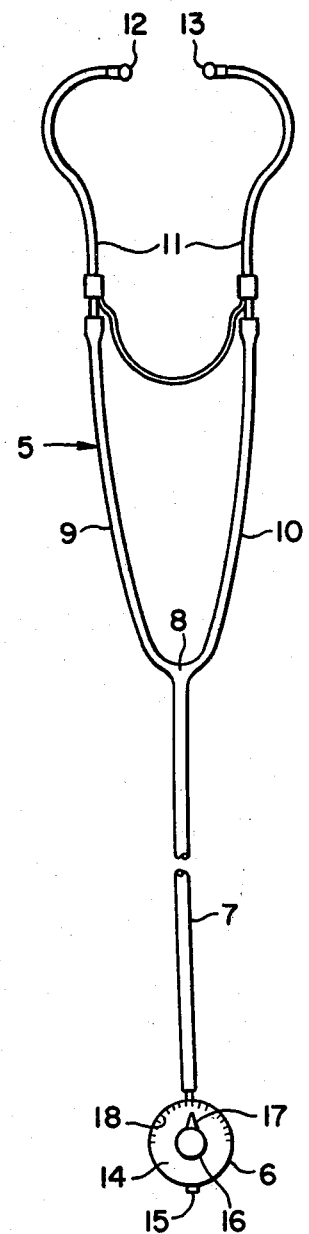
FIG. 1 is a front elevational view of a stethoscope which constitutes the presently preferred embodiment of the invention.

Referring to FIG. 1, the preferred embodiment of the invention takes the form of a stethoscope 5 which includes a pickup head 6 to which is connected a flexible tube 7. Tube 7 is bifurcated as at 8 to provide a pair of flexible conduits 9 and 10 which are connected to a typical binaural headpiece 11 having earpieces 12 and 13. The pickup head 6 is generally cylindrical in shape and includes on its backside the usual diaphragm or bell (not shown) which serves as a sensor for heart or other body sounds. Head 6 encloses a transmission space which communicates with air in the tube 7 and headpiece assembly 11.

The stethoscope 5 includes a reference impulse producer 14 for generating timed audibly detectable reference impulses which can be heard at the earpieces 12 and 13 along with the heart vibrations or body sounds sensed by the diaphragm of pickup head 6. The impulse producer 14 is shown incorporated with the pickup head 6 for maximum convenience, but it could be elsewhere on the stethoscope 5, for example at the bifurcation 8, if deemed desirable. The reference impulse producer 14 may take any suitable form known to those skilled in the art, such as mechanical, battery powered electromechanical or battery powered electronic. Winding or electric watch-type mechanisms can be used, as can microelectronic instrumentation.

The reference impulses produced by the producer 14 may be of any suitable type, whether they be in the nature of beeps, thumps, bell sounds, tones, clicks, buzzes or other sounds, so long as such impulses are detectable at the earpieces 12 and 13, do not prevent simultaneous detection of the heartbeat sound, and occur in uniformly spaced timed relation at the frequency indicated by the readout means to be described hereinafter. If deemed desirable, the producer 14 may be provided with suitable muting or volume control means (not shown) for adjustment of the sound level of the reference impulses produced thereby.

The reference impulse producer 14 is provided with a manually actuatable control button 15 for successively initiating and terminating operation thereof. Means is also provided for adjusting the frequency of the reference impulses produced by the producer 14. More particularly, the producer 14 comprises a manually adjustable member, for example a rotatable knob 16, adjustment of the position of rotation of which in one direction or the other is effective respectively to increase or decrease the frequency of the reference impulses produced. The knob 16 may, for example, be connected to a variable resistor in a microelectronic reference impulse producing circuit which produces a different frequency of reference impulse for each of various different values of resistance for which the variable resistor can be set.

The impulse producer 14 is also provided with readout means for indicating the frequency or rate of the reference impulses produced thereby per minute at each position of adjustment of the frequency adjusting member 16. In the illustrated embodiment, this readout means comprises a pointer 17 on knob 16 which cooperates with indicia 18 on the front face of pickup head 6 to indicate the frequency of impulses produced by the producer 14 at any given position of knob 16. Any suitable alternative type of readout means may be employed, including various well known types of analog or digital readout means.

The range of frequencies of reference impulses which can be produced by the producer 14 per minute should be broad enough to cover the entire range of frequencies likely to be encountered in the use of stethoscope 5. For example, in the measurement of the frequency of the human heartbeat, a range of from about thirty to about two hundred reference impulses per minute would appear to be adequate. However, for other situations wherein the pulse frequency to be measured is likely to be above or below this range, a producer 14 which is capable of producing reference impulses within such lower or higher range is employed.

The stethoscope 5 illustrated in FIG. 1 and thus far described, can be used in the normal manner by a physician, and heart or other body sounds are heard through the earpieces 12 and 13. To measure the heartbeat rate or pulse frequency of the patient, the physician actuates the control button 15 to cause the impulse producer 14 to begin producing a series of timed audible reference impulses which are heard at the earpieces 12 and 13 simultaneously with the heartbeat. The frequency of the reference impulses is determined by the position of the knob 16.

The knob 16 is then rotated, for example by the fingers of the hand which holds the pickup head 6 in place against the patient's body, in the direction and by an amount which adjusts the frequency of the reference impulses produced by producer 14 up or down as necessary to match the frequency of such impulses with the frequency of the audible heatbeat signals, i.e. to bring the rate of the reference impulses into synchrony with that of the heartbeat. When this matching is achieved, the frequency of the reference impulses, and hence the matched frequency of the heartbeat, is indicated by the readout means, i.e. the pointer 17 indicates on indicia 18 the patient's heartbeat rate. By actuation of the control button 15 the impulse producer 14 can be inactivated to terminate reference impulse generation, whereupon the stethoscope 5 is again ready for use in the conventional manner.

It is apparent that measurement of pulse frequency by the described use of the stethoscope 5 is accomplished without requiring the physician to count pulses or to give visual attention to a watch or other means for measuring time. All that is required of the physician is to adjust the knob 16 while listening, and when the reference impulses are synchronized with the heartbeat, to read the pulse frequency on the readout means.

So long as the knob 16 is not moved from is adjusted position, the pulse frequency can be read at any convenient time after the measurement has taken place. Due to the simplicity of the pulse measurement procedure described, it can be carried out by medically untrained personnel, even the patient himself.

Figure 2:
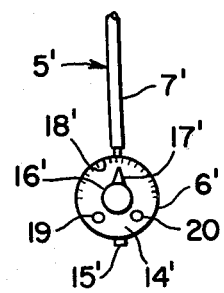
FIG. 2 is a fragmentary front elevational view similar to FIG. 1 and showing an alternative embodiment of the invention.

In FIG. 2, wherein the parts indicated by primed reference numerals correspond to parts in FIG. 1 indicated by the same numerals unprimed, a form of the invention is illustrated whose use involves observation of visual signals and reference impulses, rather than listening to audible signals and reference impulses. The stethoscope 5' in FIG. 2 is similar in all respects to stethoscope 5 in FIG. 1, except as hereinafter noted. The stethoscope 5' is provided with means for generating a visually detectable light signal corresponding to each heartbeat sensed by the diaphragm of the pickup head 6'. Any suitable or desired means known to those skilled in the art may be used for this purpose, one being conventional battery powered microelectronic circuitry (not shown) within pickup head 6' and comprising crystal pickups attached to the diaphragm thereof, for example as shown in U.S. Pat. No. 3,858,005. The electronic circuitry amplifies the signal produced by the crystal pickups and supplies electrical energy to a light emitter 19 mounted on the front face of head 6'. The light emitter 19 may take any suitable form, such as a neon bulb or a light emitting diode.

In stethoscope 5' the reference impulse producer 14' produces a series of timed visually detectable reference impulses, rather than the series of timed audibly detectable impulses produced by the producer 14 in FIG. 1. The reference impulse producer 14 may take any suitable form known to those skilled in the art, one satisfactory form of which involves battery powered electronic circuitry (not shown) connected to a light emitter 20 which is mounted on the front face of pickup head 6' near the emitter 19. The light emitter 20 may be of the same type and output as emitter 19.

The control button 15' is manually actuatable to successively initiate and terminate operation of both the circuitry associated with the emitter 19 and that associated with emitter 20. The rotatably adjustable knob 16' is controllingly connected to a component, such as a variable resistor in electronic circuitry, of producer 14', and adjustment of the position thereof in one direction or the other is effective respectively to increase or decrease the frequency of the visual reference impulses produced at emitter 20.

As with the stethoscope 5, the stethoscope 5' can be used by the physician in the normal manner to listen to the heart or other body sounds. To measure the heartbeat rate or pulse frequency of the patient, the physician actuates control button 15' to cause the circuitry for emitter 19 intermittently to energize the latter in response to heartbeats sensed by the diaphragm of pickup head 6'. Activation of control button 15' also causes the reference impulse producer 14' intermittently to energize the emitter 20 at the frequency determined by the position of knob 16'.

The knob 16 is then rotated in the direction and by an amount which adjusts the frequency of the visual reference impulses at the emitter 20 up or down as necessary to match the frequency of such impulses with the frequency of the visual heartbeat signals at emitter 19, i.e. to bring the frequency of the flashes at emitter 20 into synchrony with that of the flashes at emitter 19. When this matching is achieved, the frequency of the heartbeat measured is indicated on the readout means 17', 18' as in the form of the invention shown in FIG. 1. By activation of control button 15' the electronic circuitry associated with emitter 19 and that associated with emitter 20 are both inactivated to terminate any further flashing at said emitters, and the stethoscope 5' is again ready for use in the conventional manner.

The invention also contemplates a modification of the stethoscope 5' in which the emitter 19 and the electronic components associated therewith are not used. In use of this form of the invention the physician by adjustment of knob 16', matches the frequency of the visual reference impulses produced at emitter 20 with the frequency of the audible heartbeat signals heard through the earpieces of the stethoscope. When this matching is accomplished, the frequency of the heartbeat measured is indicated on the readout means as in the other forms of the invention.

Various other changes and modifications may be made without departing from the spirit of the invention, and all of such changes are contemplated as may come within the scope of the claims appended hereto.

What is claimed as the invention is:

1. In a stethoscope having means for conducting directly to the ears of the user heart or other body sounds of a living subject examined therewith, the improvement comprising an impulse producer capable of producing a series of timed reference impulses having a frequency range of the order of the frequency of heart pulses of living subjects and which can be detected by the stethoscope user at the same time that heart pulses of a living subject being examined with the stethoscope can be heard by such user, means including a movable member for adjusting the frequency of the reference impulses produced by the impulse producer; and readout means indicating the frequency of the impulses produced by the impulse producer at any given position of the movable member, wherefore, movement of the movable member as necessary to synchronize the frequency of the reference impulses with that of heart pulses simultaneously detected by the user causes the readout means to indicate the frequency of said heart pulses when such synchrony is achieved.

2. The stethoscope of claim 1 in which the impulse producer produces audible reference impulses.

3. The stethoscope of claim 1 wherein the impulse producer produces visual reference impulses.

4. The stethoscope of claim 1 having means for producing a series of visual signals responsive to a series of heart pulses sensed thereby, and wherein the impulse producer produces visual reference impulses.

5. A stethoscope of claim 1 wherein the position of the movable member is manually adjustable.

6. The stethoscope of claim 1 wherein the impulse producer and readout means are incorporated with the pickup head of the stethoscope.

7. The stethoscope of claim 1 having means for producing a series of visual signals responsive to a series of heart pulses sensed thereby, and the impulse producer includes means for producing visual reference impulses at a position juxtaposed to that at which said visual signals are produced.

8. The stethoscope of claim 1 having means for manually activating and deactivating the impulse producer.

* * * * *